US009728388B2

United States Patent
Naya et al.

(10) Patent No.: US 9,728,388 B2
(45) Date of Patent: Aug. 8, 2017

(54) MEASUREMENT DEVICE, MEASUREMENT APPARATUS, AND METHOD

(71) Applicant: FUJIFILM Corporation, Tokyo (JP)

(72) Inventors: Masayuki Naya, Ashigarakami-gun (JP); Shogo Yamazoe, Ashigarakami-gun (JP); Megumi Shiota, Ashigarakami-gun (JP); Makoto Suematsu, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 143 days.

(21) Appl. No.: 14/875,129

(22) Filed: Oct. 5, 2015

(65) Prior Publication Data

US 2016/0027631 A1 Jan. 28, 2016

Related U.S. Application Data

(63) Continuation of application No. PCT/JP2014/001985, filed on Apr. 7, 2014.

(30) Foreign Application Priority Data

Apr. 8, 2013 (JP) .................................. 2013-080164

(51) Int. Cl.
*G01N 21/00* (2006.01)
*H01J 49/16* (2006.01)
(Continued)

(52) U.S. Cl.
CPC .......... *H01J 49/164* (2013.01); *G01N 21/658* (2013.01); *H01J 49/0004* (2013.01);
(Continued)

(58) Field of Classification Search
CPC ........ G01N 21/64; G01N 21/65; G01N 21/63; G01N 21/658; G01N 21/648; H01J 49/16; H01J 49/04
See application file for complete search history.

(56) References Cited

U.S. PATENT DOCUMENTS

| 5,955,729 A | 9/1999 | Nelson et al. |
| 2007/0158549 A1 | 7/2007 | Naya et al. |

(Continued)

FOREIGN PATENT DOCUMENTS

| JP | 3930563 B2 | 6/2007 |
| JP | 2007-171003 A | 7/2007 |

(Continued)

OTHER PUBLICATIONS

Japanese Office Action, issued Jun. 28, 2016, for Japanese Application No. 2013-080164, together with an English translation thereof.

(Continued)

*Primary Examiner* — Abdullahi Nur
(74) *Attorney, Agent, or Firm* — Birch, Stewart, Kolasch & Birch, LLP

(57) ABSTRACT

A metal film of a measurement device including a transparent dielectric substrate is irradiated with first light from a transparent dielectric substrate side, an optical electric field enhanced by an optical electric field enhancing effect of a localized plasmon induced to a surface of the metal film by the irradiation is generated, light emitted from the transparent dielectric substrate side is detected, a specimen installed on a surface of a metal fine concavo-convex structure layer and a matrix agent are irradiated with second light from a side opposite to the side of the irradiation with the first light in a state where a voltage is applied to the metal fine concavo-convex structure layer through a voltage application electrode, an analysis target substance for mass spectrometry in the specimen is desorbed from the surface by the irradiation, and the desorbed analysis target substance is detected.

12 Claims, 7 Drawing Sheets

(51) Int. Cl.
  *G01N 21/65* (2006.01)
  *H01J 49/00* (2006.01)
  *H01J 49/04* (2006.01)
  *H01J 49/40* (2006.01)

(52) U.S. Cl.
  CPC .... *H01J 49/0418* (2013.01); *G01N 2201/068* (2013.01); *G01N 2201/06113* (2013.01); *H01J 49/40* (2013.01)

(56) References Cited

U.S. PATENT DOCUMENTS

| | | |
|---|---|---|
| 2008/0290272 A1 | 11/2008 | Naya et al. |
| 2008/0304060 A1 | 12/2008 | Naya |
| 2009/0238723 A1 | 9/2009 | Guharay |
| 2011/0266438 A1 | 11/2011 | Harada et al. |
| 2012/0038926 A1* | 2/2012 | Endo ............... B82Y 20/00 356/445 |
| 2013/0182248 A1 | 7/2013 | Naya et al. |

FOREIGN PATENT DOCUMENTS

| | | |
|---|---|---|
| JP | 2008-107209 A | 5/2008 |
| JP | 2008-304370 A | 12/2008 |
| JP | 2011-232180 A | 11/2011 |
| JP | 2011-246307 A | 12/2011 |
| JP | 2012-063294 A | 3/2012 |
| JP | 2012-117245 A | 6/2012 |
| JP | 2012-181022 A | 9/2012 |
| JP | 5069497 B2 | 11/2012 |
| WO | WO 2014/050133 A1 | 4/2014 |

OTHER PUBLICATIONS

International Search Report issued in PCT/JP2014/001985 dated Aug. 12, 2014.

Written Opinion of the Internatibnal Searching Authority (PCT/ISA/237) issued in PCT/JP2014/001985 dated Aug. 12, 2014.

* cited by examiner

MEASUREMENT DEVICE, MEASUREMENT APPARATUS, AND METHOD

CROSS-REFERENCE TO RELATED APPLICATIONS

This application is a Continuation of PCT International Application No. PCT/JP2014/001985 filed on Apr. 7, 2014, which claims priority under 35 U.S.C. §119(a) to Japanese Patent Application No. 2013-080164 filed on Apr. 8, 2013. Each of the above applications is hereby expressly incorporated by reference, in its entirety, into the present application.

BACKGROUND OF THE INVENTION

1. Field of the Invention

The present invention relates to a measurement device used for both optical measurement and mass spectrometry, a measurement apparatus that performs both optical measurement and mass spectrometry using the measurement device, and a measurement method.

2. Description of the Related Art

Hitherto, as an analysis method used for the identification of a substance, and the like, there has been known a mass spectrometry method in which an analysis target substance which adheres to the surface of a substrate is desorbed from the surface of the substrate and is ionized, thereby identifying the substance on the basis of a ratio of the mass of the substance to an electric charge (see JP5069497B, JP2012-117245A, and JP2008-107209A). For example, in time-of-flight mass spectroscopy (TOF-MS), an ionized analysis target substance is flown by a predetermined distance between high voltage electrodes, and the mass of the substance is analyzed on the basis of a flight time thereof.

A method of desorbing and ionizing an analysis target substance in such a mass spectrometry method includes a laser desorption/ionization method utilizing laser irradiation, and a surface-enhanced laser desorption/ionization (SELDI) method has been proposed as the laser desorption/ionization method.

The SELDI method is a method of capturing an analysis target substance, having a specific property, which is present in a specimen, on a chip using a chemical functional group and molecules which are fixed to the surface of the chip, refining the analysis target substance, and then desorbing and ionizing the captured analysis target substance by performing laser irradiation.

On the other hand, similarly to the above-mentioned mass spectrometry of a substance, a Raman spectroscopy method is known as a method of performing the identification of a substance. The Raman spectroscopy method is a method of obtaining a spectrum of Raman scattered light (Raman spectrum) by separating scattered light obtained by irradiating a substance with single wavelength light, and can include analyzing the spectrum for the identification of the substance.

The above-mentioned Raman spectroscopy method includes so-called surface enhanced Raman (SERS) using an optical electric field which is enhanced by localized plasmon resonance in order to enhance feeble Raman scattered light.

This method uses a principle in which when a metal body, particularly, a metal body having nano-order irregularities in the surface thereof is irradiated with light in a state where the metal body is brought into contact with a substance, an optical electric field is enhanced by localized plasmon resonance, and the intensity of Raman scattered light of a specimen coming into contact with the surface of the metal body is enhanced.

SUMMARY OF THE INVENTION

Here, the above-mentioned mass spectrometry method is a method of desorbing an analysis target substance from the surface of a substrate by irradiating a specimen with a laser and ionizing the substance. Accordingly, for example, when the specimen is a biological cell, information of the total amount of substances including the inside and surface of the cell is obtained.

On the other hand, the above-mentioned SERS method is a method of detecting the intensity of Raman scattered light of a specimen coming into contact with the surface of a metal body, and thus information of the vicinity of a contact surface between the specimen and the surface of the metal body is acquired. Accordingly, for example, it is possible to acquire information of a metabolite or the like which oozes out from the cell and adheres to the surface of the metal body and to expect to acquire information different from that in the mass spectrometry method.

However, when measurement is performed on the same specimen, for example, using both the SELDI method and SERS method mentioned above, it is necessary to firmly fix the specimen onto a substrate in a very small amount of molecular order in the SELDI method. Accordingly, it is not possible to perform measurement using a thick cell that releases the above-mentioned metabolite, as a specimen.

In addition, when the measurement is performed by the SELDI method, the entire specimen on the substrate is desorbed and disappears by the measurement, and thus the measurement by the SERS method may not be performed thereafter.

Meanwhile, in JP5069497B, JP2012-117245A, and JP2008-107209A mentioned above, nothing related to the execution of both mass spectrometry and optical measurement such as a SERS method is proposed.

The present invention is contrived in view of such situations, and an object thereof is to provide a measurement device capable of performing both mass spectrometry and optical measurement such as a SERS method using the same specimen to thereby acquire both information of the total amount of substances of the specimen and information of the vicinity of the surface of the specimen, a measurement apparatus using the measurement device, and a measurement method.

According to an aspect of the invention, there is provided a measurement device including a transparent dielectric substrate that is constituted of a dielectric having a transparent fine concavo-convex structure in a surface thereof, and a metal fine concavo-convex structure layer that is configured by forming a metal film on a surface of the fine concavo-convex structure, in which the metal fine concavo-convex structure layer allows electrical conduction within the metal fine concavo-convex structure layer, and a voltage application electrode for applying a voltage to the metal fine concavo-convex structure layer is provided.

In addition, in the above-mentioned measurement device of the present invention, a surface resistivity of a metal fine concavo-convex structure layer may be set to be equal to or less than $10^7$ Ω/cm.

In addition, the fine concavo-convex structure may be formed of boehmite.

In addition, the metal film may be formed of at least one metal selected from a group consisting of Au, Ag, Cu, Al, Pt, and an alloy containing the metal as a main component.

In addition, a position marker for indicating a measurement position may be provided.

In addition, the position marker may be provided in the voltage application electrode.

In addition, the position marker may be a void provided in the voltage application electrode.

According to another aspect of the invention, there is provided a measurement apparatus including the measurement device according to the aspect, a first light irradiation unit that irradiates the metal film of the measurement device with first light from the transparent dielectric substrate side and generates an enhanced optical electric field on a surface of the metal film by an optical electric field enhancing effect of a localized plasmon induced to the surface by the irradiation, a light detection unit that detects light which is generated by the irradiation of the measurement device with the first light and which is emitted from the transparent dielectric substrate side, a second light irradiation unit that irradiates a specimen installed on a surface of the metal fine concavo-convex structure layer and a matrix agent supplied onto the specimen with second light from a side opposite to the side of the irradiation with the first light in a state where a voltage is applied to the metal fine concavo-convex structure layer through the voltage application electrode, and desorbs an analysis target substance for mass spectrometry in the specimen from the surface by the irradiation and an analysis unit that detects the desorbed analysis target substance to thereby analyze the mass of the analysis target substance.

In addition, the above-mentioned measurement apparatus of the present invention may further include a scanning mechanism that two-dimensionally scans an upper portion of the measurement device with the first light and the second light.

In addition, when a measurement device provided with the above-mentioned position marker is used as the measurement device, the measurement apparatus may further include a positioning unit that performs the positioning of an optical spectrum distribution image generated on the basis of a detection result of a light detection unit and a mass spectrum distribution image generated on the basis of an analysis result of an analysis unit, on the basis of a detection result of the position marker provided in the measurement device.

In addition, the measurement apparatus may further include a voltage application unit that applies a voltage to the voltage application electrode of the measurement device.

According to still another aspect of the invention, there is provided a measurement method including irradiating the metal film of the measurement device according to the aspect with first light from the transparent dielectric substrate side, detecting light emitted from the transparent dielectric substrate side by generating an enhanced optical electric field on a surface of the metal film by an optical electric field enhancing effect of a localized plasmon induced to the surface by the irradiation, irradiating a specimen installed on a surface of the metal fine concavo-convex structure layer and a matrix agent supplied onto the specimen with second light from a side opposite to the side of the irradiation with the first light in a state where a voltage is applied to the metal fine concavo-convex structure layer through the voltage application electrode, desorbing an analysis target substance for mass spectrometry in the specimen from the surface by the irradiation, and detecting the desorbed analysis target substance to thereby analyze the mass of the analysis target substance.

According to the measurement device, the measurement apparatus, and the measurement method of the present invention, it is possible to irradiate a metal film of the measurement device including a transparent dielectric substrate with first light from the transparent dielectric substrate side, to detect light emitted from the transparent dielectric substrate side by generating an enhanced optical electric field on a surface of the metal film by an optical electric field enhancing effect of a localized plasmon induced to the surface by the irradiation, to irradiate a specimen installed on a surface of a metal fine concavo-convex structure layer and a matrix agent supplied onto the specimen with second light from a side opposite to the side of the irradiation with the first light in a state where a voltage is applied to the metal fine concavo-convex structure layer through a voltage application electrode, to desorb an analysis target substance for mass spectrometry in the specimen from the surface by the irradiation, and to detect the desorbed analysis target substance to thereby analyze the mass of the analysis target substance.

That is, according to the measurement device, the measurement apparatus, and the measurement method of the present invention, both mass spectrometry and optical measurement such as a SERS method can be performed using the same specimen, and thus it is possible to acquire both information of the total amount of substances of the specimen and information of the vicinity of the surface of the specimen.

When adenosine triphosphate (ATP) is measured by combining the two pieces of information with each other and using a tissue such as, for example, a brain of a mouse as a specimen, it is possible to obtain information regarding not only the amount of substance inside the tissue but also the easiness of holding of the substance by the tissue.

In addition, a so-called matrix assisted laser desorption/ionization (MALDI) method in which mass spectrometry is performed by supplying a matrix agent onto a specimen is used, and thus it is possible to measure a relatively thick sample. Thereby, it is possible to prevent the specimen from being burned up after the mass spectrometry and to continuously perform optical measurement such as a SERS method.

DESCRIPTION OF THE PREFERRED EMBODIMENTS

Figure 1:
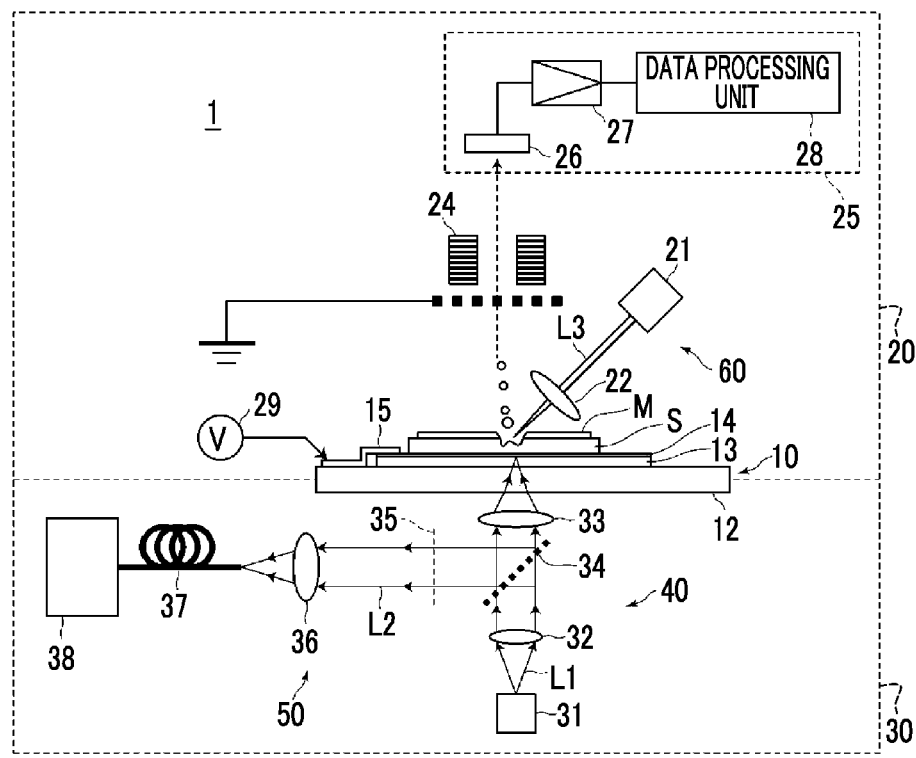
FIG. 1 is a diagram illustrating a schematic configuration of a measurement apparatus according to an embodiment of the present invention.

Hereinafter, a measurement device, a measurement apparatus, and a measurement method of the present invention will be described in detail with reference to the accompanying drawings. FIG. 1 is a block diagram illustrating a schematic configuration of a measurement apparatus 1 of the present embodiment.

The measurement apparatus 1 of the present embodiment performs irradiation with excitation light from the back side (transparent dielectric substrate 11 side) of the measurement device 10, detects a Raman scattered light emitted from a transparent dielectric substrate 11 of the measurement device 10 by generating an enhanced optical electric field on the surface of a metal film by an optical electric field enhancing effect of a localized plasmon induced to the surface by the irradiation with the excitation light, irradiates a specimen installed on the surface of a metal fine concavo-convex structure layer 14 of the measurement device 10 with measurement light from the specimen side, desorbs an analysis target substance for mass spectrometry in the specimen from the surface, and detects the desorbed analysis target substance to thereby analyze the mass of the analysis target substance. That is, the measurement apparatus 1 of the present embodiment can detect the Raman scattered light of the specimen installed in the measurement device 10 and perform mass spectrometry of the analysis target substance in the same specimen.

As illustrated in FIG. 1, the measurement apparatus 1 includes the measurement device 10 on which a specimen S is installed, a measurement system 20 that performs mass spectrometry of the specimen S, and a measurement system 30 that measures Raman scattered light of the specimen S.

Figure 2:
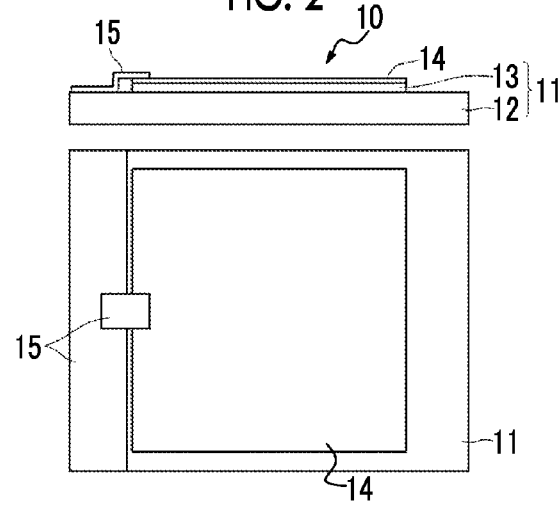
FIG. 2 is a side cross-sectional view and a top view of a measurement device according to the embodiment of the present invention.

First, the measurement device 10 of the present embodiment will be described. FIG. 2 illustrates a side cross-sectional view (upper diagram) and a top view (lower diagram) of the measurement device 10 of the present embodiment.

As illustrated in FIG. 2, the measurement device 10 includes a transparent dielectric substrate 11 including a fine concavo-convex structure 13 on the surface thereof, a metal fine concavo-convex structure layer 14 which is configured by forming a metal film on the surface of the fine concavo-convex structure 13, and a voltage application electrode 15 for applying a voltage to the metal fine concavo-convex structure layer 14.

In the measurement device 10, the metal film of the metal fine concavo-convex structure layer 14 is irradiated with excitation light L1 to thereby induce localized plasmon resonance, and an enhanced optical electric field is generated on the surface of the metal film by the localized plasmon resonance.

The transparent dielectric substrate 11 includes a substrate body 12 constituted by a transparent dielectric such as glass, and the fine concavo-convex structure 13 formed of a material different from that of the substrate body 12. Meanwhile, the term "transparent" used herein refers to transmissivity with respect to excitation light and Raman scattered light being equal to or higher than 50%, preferably, equal to or higher than 75%, and further preferably equal to or higher than 90%.

The fine concavo-convex structure 13 in the present embodiment is formed of boehmite. The fine concavo-convex structure 13 is formed such that an average of the depth and an average of the pitch of a convex portion of the metal fine concavo-convex structure layer 14 on the surface thereof become shorter than the wavelength of the excitation light L1, and may be able to generate a localized plasmon on the surface of the metal fine concavo-convex structure layer 14. In particular, in the fine concavo-convex structure 13, an average of the depth between the top of a convex portion and the bottom of an adjacent concave portion is preferably equal to or less than 200 nm, and an average of the pitch between the tops of most adjacent convex portions with a concave portion interposed therebetween is preferably equal to or less than 200 nm.

The metal fine concavo-convex structure layer 14 may be formed of a metal capable of generating a localized plasmon by being irradiated with excitation light. For example, the metal fine concavo-convex structure layer is formed of at least one metal selected from the group consisting of Au, Ag, Cu, Al, Pt, and an alloy containing the metal as a main component. In particular, Au or Ag is preferable.

The thickness of the metal fine concavo-convex structure layer 14 is not particularly limited insofar as the metal fine concavo-convex structure layer has such a thickness that an irregular shape capable of generating a localized plasmon by being irradiated with excitation light can be maintained as a metal fine concavo-convex structure, when being formed on the surface of the fine concavo-convex structure 13, and is preferably 10 nm to 100 nm.

The metal fine concavo-convex structure layer 14 is applied with a voltage during the mass spectrometry mentioned above, and has a conductive property. The surface resistivity of the metal fine concavo-convex structure layer 14 is preferably equal to or less than $10^7$ Ω/cm. The surface resistivity is a value measured by putting a probe on any two points of the metal fine concavo-convex structure layer 14 and the voltage application electrode 15, using a tester.

The voltage application electrode 15 is connected to the metal fine concavo-convex structure layer 14, and is used to apply a voltage to the metal fine concavo-convex structure layer 14. The voltage application electrode 15 is formed of, for example, Cr, Au, Al, or Ag.

Figure 3:
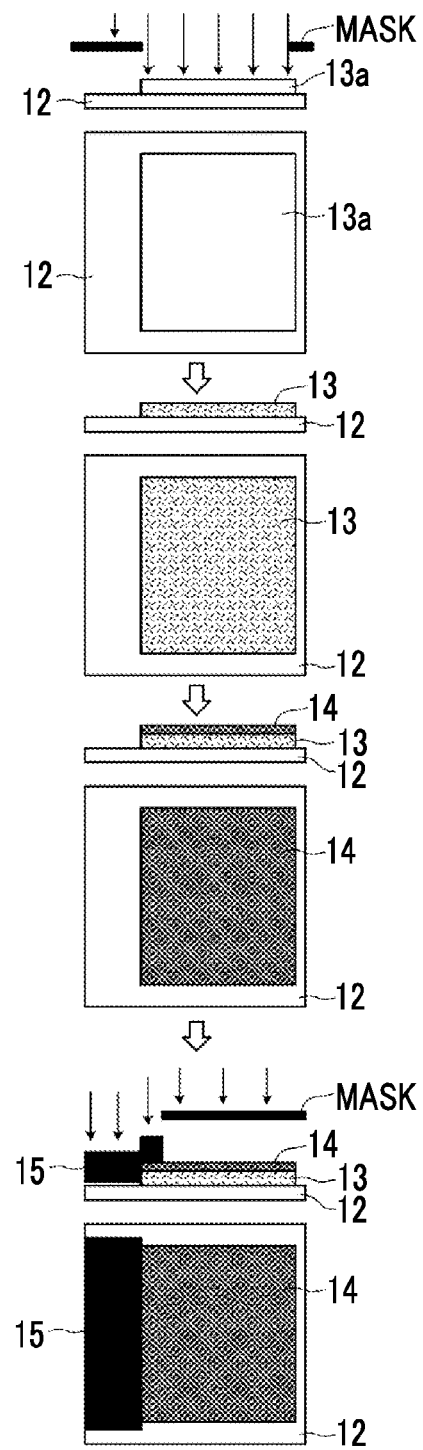
FIG. 3 is a diagram illustrating each process of a manufacturing method of the measurement device according to the embodiment of the present invention.

Here, a method of manufacturing the measurement device 10 in the present embodiment will be described with reference to FIG. 3. FIG. 3 illustrates a side cross-sectional view (upper diagram) and a top view (lower diagram) in each manufacturing process of the measurement device 10.

First, the plate-like substrate body 12 is prepared, and the substrate body 12 is cleaned with pure water. Thereafter, aluminum 13a is formed on the surface of the substrate body 12 so as to have a thickness of approximately several tens of nm by a sputtering method using a mask.

Thereafter, the substrate body 12 with the aluminum 13a is immersed in the pure water during the boiling of the pure water, and is taken out after several minutes (approximately 5 minutes). The aluminum 13a is made transparent by the boiling treatment (boehmite treatment), thereby forming the fine concavo-convex structure 13.

Figure 4:
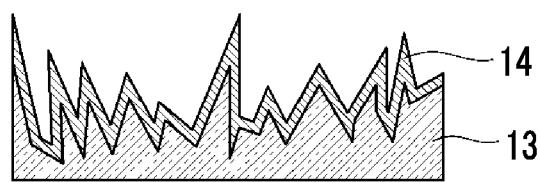
FIG. 4 is a partially enlarged view of a fine concavo-convex structure and a metal fine concavo-convex structure layer.

Next, a metal film is vapor-deposited on the fine concavo-convex structure 13. The metal film is formed along the fine concavo-convex structure 13, thereby configuring the metal fine concavo-convex structure layer 14. FIG. 4 is a partially enlarged view in a state where the metal fine concavo-convex structure layer 14 is formed on the fine concavo-convex structure 13. Meanwhile, as described above, the metal fine concavo-convex structure layer 14 is formed to have a conductive property, but a metal fine concavo-convex structure layer having a surface resistivity of $10^{-1}$ Ω/cm can be manufactured as an example.

Subsequently, an electrode material is formed on a partial range of the surface of the substrate body 12 and an end of the surface of the metal fine concavo-convex structure layer 14 on which the fine concavo-convex structure 13 and the metal fine concavo-convex structure layer 14 are not formed, by a sputtering method using a mask, thereby forming the voltage application electrode 15.

Meanwhile, as a metal to be subjected to a hydrothermal reaction in a fine concavo-convex structure manufacturing process through the above-mentioned boiling treatment, a metal oxide such as alumina $(Al(OH)_3)$ may be used instead of the above-mentioned aluminum. The aluminum and the alumina can form a fine concavo-convex structure having a complicated triangular pyramid structure formed of either one or both of bayerite $(Al[OH]_3)$ and boehmite (AlOOH) by a hydrothermal reaction on a substrate. Meanwhile, in addition to aluminum, a metal such as titanium (Ti) which similarly forms a fine concavo-convex structure by a hydrothermal reaction can be used.

In addition, a method of forming a metal or a metal oxide on the substrate body 12 is not limited to the sputtering method, and a heating deposition method or a sol-gel method may be used.

In addition, the hydrothermal reaction is not limited to the boiling treatment, and a treatment of exposing a substrate having a metal or a metal oxide formed thereon to high-temperature water vapor to react the metal or the metal oxide with the high-temperature water vapor may be performed.

In addition, the fine concavo-convex structure 13 may be formed of a transparent material other than boehmite. For example, the transparent dielectric substrate 11 may be configured by performing an anodic oxidation treatment on an aluminum substrate to manufacture anodic oxidation alumina having a large number of micropores on the upper layer portion thereof, setting anodic oxidation alumina, obtained by removing an aluminum portion which is not anodically oxidized, to be the fine concavo-convex structure 13, and fixing the fine concavo-convex structure onto the substrate body 12 such as glass.

In addition, the fine concavo-convex structure may be formed of not only a material different from that of the substrate body but also the same material as that of the substrate body by processing the surface of the substrate body. For example, a glass substrate having a fine concavo-convex structure formed by processing the surface thereof by lithography and dry etching may be used as the transparent dielectric substrate.

Next, referring back to FIG. 1, a mass spectrometry measurement system 20 in the measurement apparatus 1 of the present embodiment will be described. The mass spectrometry measurement system 20 is a so-called time-of-flight mass spectrometer (TOF-MS).

The mass spectrometry measurement system 20 includes a measurement light irradiation unit 60 (second light irradiation unit) that irradiates a specimen S installed on the surface of the metal fine concavo-convex structure layer 14 of the measurement device 10 and a matrix agent M supplied onto the specimen S with measurement light L3 (second light) to thereby desorb an analysis target substance for mass spectrometry in the specimen from the surface of the measurement device 10, and an analysis unit 25 that detects the desorbed analysis target substance to thereby analyze the mass of the analysis target substance.

In addition, a drawing grid 23 disposed at a position facing the surface of the measurement device 10 and an end plate 24 disposed so as to face a surface of the drawing grid 23 which is opposite to a surface on the measurement device 10 side are provided between the measurement device 10 and the analysis unit 25.

In addition, a voltage application unit 29 that applies a voltage to the voltage application electrode 15 of the measurement device 10 is included.

The measurement light irradiation unit 60 includes a semiconductor laser light source 21 that emits the measurement light L3, and a light condensing optical system 22 that condenses the measurement light L3 emitted from the semiconductor laser light source 21 on a specimen. For example, a pulse laser beam having a wavelength of 337 nm and a pulse width of approximately 50 ps to 50 ns can be used as the measurement light L3.

The analysis unit 25 includes a detector 26 that detects an analysis target substance which is desorbed from the surface of the measurement device 10 by the irradiation with the measurement light L3 and which is flown through center holes of the drawing grid 23 and the end plate 24, an amplifier 27 that amplifies an output of the detector 26, and a data processing unit 28 that processes an output signal from the amplifier 27.

Next, a Raman scattered light measurement system 30 in the measurement apparatus 1 of the present embodiment will be described.

As illustrated in FIG. 1, the Raman scattered light measurement system 30 includes an excitation light irradiation unit 40 (first light irradiation unit) that performs irradiation with the excitation light L1 (first light) from the back side of the measurement device 10 (the transparent dielectric substrate 11 side), and a light detection unit 50 for detecting Raman scattered light L2 which is emitted from a substance in the vicinity of the metal fine concavo-convex structure layer 14 of the measurement device 10 and is enhanced by an optical electric field enhancing effect from the back side of the measurement device 10.

The excitation light irradiation unit 40 includes a semiconductor laser light source 31 that emits the excitation light L1, a lens 32 that converts the excitation light L1 emitted from the semiconductor laser light source 31 into parallel light, a half mirror 34 that transmits the excitation light L1 converted into parallel light by the lens 32 and reflects light including the Raman scattered light L2 emitted from the substance in the vicinity of the metal fine concavo-convex structure layer 14 of the measurement device 10 to the light detection unit 50 side by the irradiation with the excitation light L1, and a lens 33 that condenses the excitation light L1 having passed through the half mirror 34 on the vicinity of the metal fine concavo-convex structure layer 14 and converts the Raman scattered light L2 into parallel light.

The light detection unit 50 includes a notch filter 35 that removes the excitation light L1 in the light reflected by the half mirror 34 and transmits the other light beams, a lens 36 for condensing the Raman scattered light L2 having passed through the notch filter 35, a light guiding unit 37 that guides the Raman scattered light L2 condensed by the lens 36 to a spectroscope 38, and the spectroscope 38 that detects the Raman scattered light L2 guided by the light guiding unit 37.

Next, mass spectrometry using the mass spectrometry measurement system 20 of the measurement apparatus 1 of the present embodiment and the detection of Raman scattered light using the Raman scattered light measurement system 30 will be described.

Figure 5:
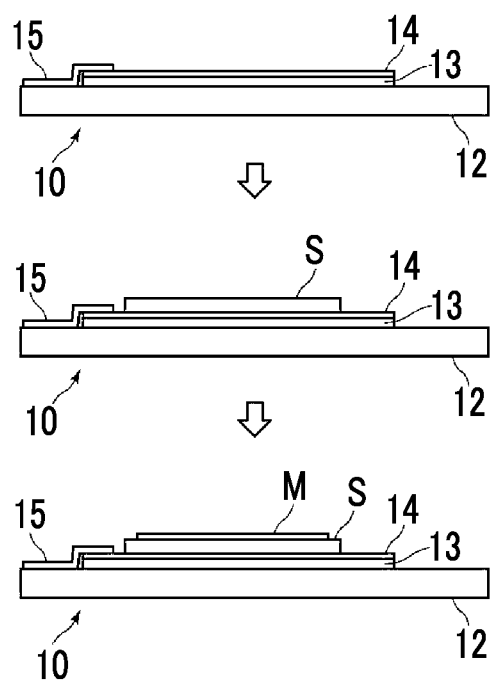
FIG. 5 is a diagram illustrating a specimen S and a matrix agent M which are objects to be measured.

First, as illustrated in FIG. 5, the measurement device 10 of the present embodiment is prepared, the specimen S including an analysis target substance for mass spectrometry is supplied onto the surface of the metal fine concavo-convex structure layer 14 of the measurement device 10, and the matrix agent M is supplied onto the specimen S.

The matrix agent M absorbs the measurement light L3 and converts the absorbed measurement light into thermal energy, an analysis target substance in the specimen S is vaporized together with the matrix agent M by the thermal energy, and the analysis target substance is ionized by proton transfer occurring between the matrix agent M and the analysis target substance. First, a specimen including a mixture of a specimen containing an analysis target substance A and the matrix agent M is prepared as the specimen S.

A well-known matrix agent, which has been used in a MALDI method of the related art, can be used as the matrix agent M. Specifically, nicotinic acid, picolinic acid, 3-hydroxy picolinic acid, 3-amino-picolinic acid, 2,5-dihydroxybenzoic acid, α-cyano-4-hydroxycinnamic acid, sinapic acid, 2-(4-hydroxyphenylazo)benzoic acid, 2-mercaptobenzothiazole, 5-chloro-2-mercaptobenzothiazole, 2,6-dihydroxyacetophenone, 2,4,6-trihydroxyacetophenone, dithranol, benzo[a]pyrene, 9-nitro-anthracene, 2-[(2E)-3-(4-tret-butylphenyl)-2-methylprop-2-eniriden]maroninitrile, or the like can be used as the matrix agent M.

The voltage application unit 29 applies a predetermined voltage to the voltage application electrode 15 of the measurement device 10 which is supplied with the specimen S and the matrix agent M, and the measurement light irradiation unit 60 irradiates the surface of the measurement device 10 with the measurement light L3. The measurement light L3 is absorbed into the matrix agent M and is converted into thermal energy, and an analysis target substance in the specimen S is vaporized together with the matrix agent M by the thermal energy, is desorbed from the surface of the measurement device 10, and is ionized at the same time.

The desorbed analysis target substance is detected by being drawn out in a direction of the drawing grid 23 by a potential difference between the metal fine concavo-convex structure layer 14 of the measurement device 10 which is applied with a voltage and the drawing grid 23 which is grounded, being accelerated, being substantially rectilinearly flown in a direction of the end plate 24 through the center hole of the drawing grid, and passing through the hole of the end plate 24 to reach the detector 26.

A flight speed of the desorbed analysis target substance depends on the mass of the substance and becomes higher as the mass becomes smaller, and thus the substance is detected by the detector 26 in ascending order of mass.

An output signal from the detector 26 is amplified to a predetermined level by the amplifier 27 and is then input to the data processing unit 28. The data processing unit 28 measures a flight time of an analysis target substance on the basis of the output signal from the amplifier 27, and obtains a mass spectrum by deriving mass from the flight time.

Next, a description will be given of a method of measuring a Raman spectrum of a metabolite or the like which is discharged from the specimen S using the Raman scattered light measurement system 30 of the measurement apparatus 1 of the present embodiment. Meanwhile, the measurement of the Raman spectrum may be performed simultaneously with the above-mentioned mass spectrometry, or may be performed before or after the mass spectrometry.

First, the semiconductor laser light source 31 of the excitation light irradiation unit 40 emits the excitation light L1 toward the measurement device 10 supplied with the specimen S and the matrix agent M in the above-mentioned manner, and the excitation light L1 passes through the lens 32 and the half mirror 34, is condensed by the lens 33, and is emitted to the vicinity of the metal fine concavo-convex structure layer 14 on the measurement device 10.

Localized plasmon resonance is induced in the metal fine concavo-convex structure layer 14 by the irradiation with the excitation light L1, and an enhanced optical electric field is generated on the surface of the metal fine concavo-convex structure layer 14. In addition, the Raman scattered light L2 which is emitted from a substance in the vicinity of the metal fine concavo-convex structure layer 14 and is enhanced by the optical electric field passes through the lens 33 and is reflected to the spectroscope 38 side by the half mirror 34. Meanwhile, at this time, the excitation light L1 reflected by the measurement device 10 is also reflected by the half mirror 34 and is reflected to the spectroscope 38 side, but the excitation light L1 is removed by the notch filter 35.

On the other hand, light having a wavelength different from that of the excitation light L1 passes through the notch filter 35, and is condensed on the light guiding unit 37 by the lens 36. The light condensed by the light guiding unit 37 is incident on the spectroscope 38, and Raman spectrum measurement is performed by the spectroscope 38.

According to the measurement apparatus 1 of the above-described embodiment, both mass spectrometry and optical measurement such as a SERS method can be performed using the same specimen, and thus it is possible to acquire both information of the total amount of substances of the specimen and information of the vicinity of the surface of the specimen.

When adenosine triphosphate (ATP) is measured by combining the two pieces of information with each other and using a tissue such as, for example, a brain of a mouse as a specimen, it is possible to obtain information regarding not only the amount of substance inside the tissue but also the easiness of holding of the substance by the tissue.

In addition, a so-called MALDI method in which mass spectrometry is performed by supplying a matrix agent onto a specimen is used, and thus it is possible to measure a relatively thick sample. Thereby, it is possible to prevent the specimen from being burned up after the mass spectrometry and to continuously perform optical measurement such as a SERS method.

In addition, in the measurement apparatus 1 of the above-described embodiment, an upper portion of the specimen S may be two-dimensionally scanned with the excitation light L1 and the measurement light L3 so as to acquire a Raman spectrum with respect to each scanning point of the excitation light L1 on the specimen S and to acquire a mass spectrum with respect to each scanning point of the measurement light L3 on the specimen.

Figure 6:
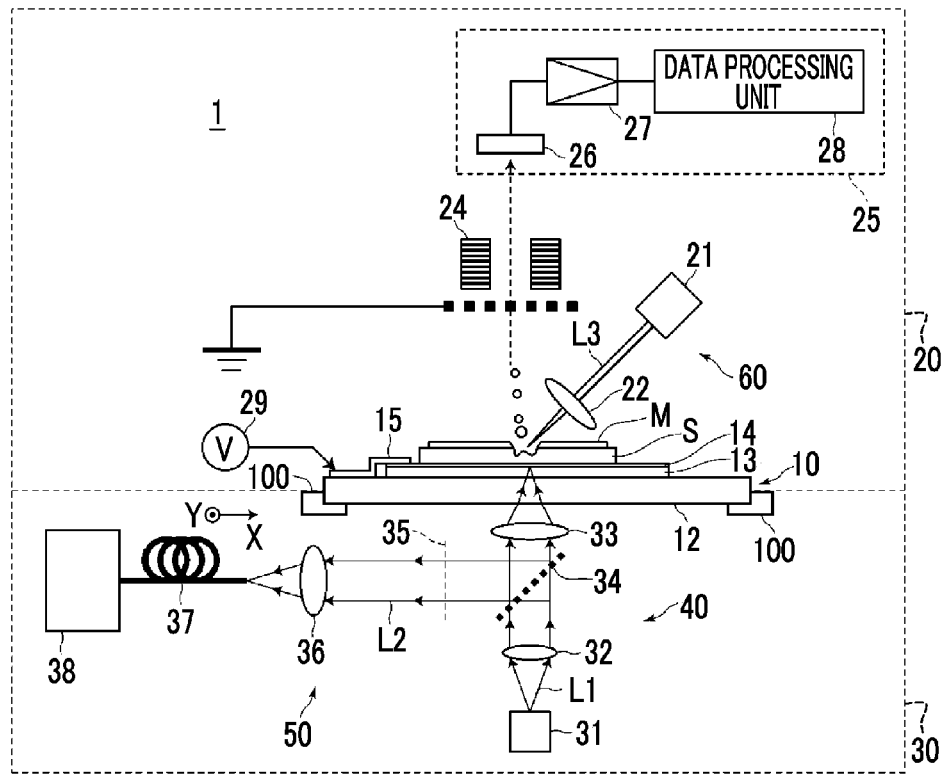
FIG. 6 is a diagram illustrating a schematic configuration of a measurement apparatus according to another embodiment of the present invention.

Specifically, for example, as illustrated in FIG. 6, in the measurement apparatus 1 of the above-described embodiment, a movement stage 100 that holds the measurement device 10 and moves the measurement device 10 in an X direction and a Y direction (thickness direction of the paper) which are illustrated in FIG. 6 may be provided so that the measurement device 10 is moved by the movement stage 100, thereby two-dimensionally scanning the measurement device 10 with the excitation light L1 and the measurement light L3.

Meanwhile, a scanning mechanism performing two-dimensionally scanning with the excitation light L1 and the measurement light L3 is not limited thereto, and the measurement device 10 may be two-dimensionally scanned with the excitation light L1 and the measurement light L3 by setting the measurement device 10 to be in a fixed state and using, for example, a galvanometer mirror.

In addition, the mass spectrometry measurement system 20 and the Raman scattered light measurement system 30 in the measurement apparatus 1 of the above-described embodiment may be integrally formed as illustrated in FIGS. 1 and 6, or may be separately formed.

When the mass spectrometry measurement system 20 and the Raman scattered light measurement system 30 are integrally formed, components of the mass spectrometry measurement system 20 other than at least the amplifier 27 and the data processing unit 28 and each component of the Raman scattered light measurement system 30 are disposed within a vacuum box which is set to be in a vacuum state.

In addition, when the above-mentioned mass spectrometry measurement system 20 and Raman scattered light measurement system 30 are separately formed, components of the mass spectrometry measurement system 20 other than at least the amplifier 27 and the data processing unit 28 are disposed within a vacuum box, and mass spectrometry and the detection of Raman scattered light are performed using the same measurement device 10.

Here, as described above, when the measurement systems are separately formed, or measurements in the respective measurement systems are performed at individual timings in a configuration in which the measurement systems are integrally formed, it is necessary to make measurement positions in the respective measurement systems coincide with each other at the time of performing measurement by two-dimensionally scanning the measurement device 10 as described above.

Consequently, a position marker may be provided in the measurement device 10, and the measurement positions in the respective measurement systems may be made to coincide with each other using a detection result of the position marker.

Figure 7:
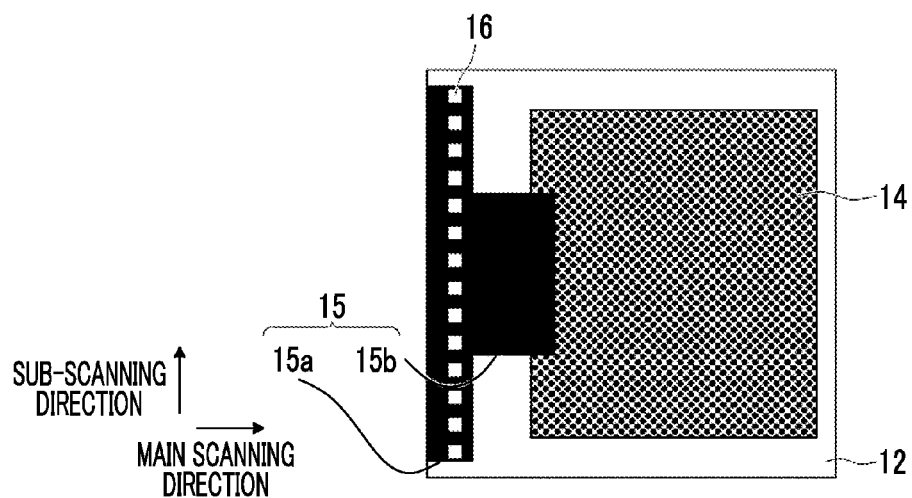
FIG. 7 is a top view of a measurement device according to another embodiment of the present invention.

FIG. 7 illustrates an example in which position markers 16 are formed in the voltage application electrode 15 of the measurement device 10. In the measurement device 10 illustrated in FIG. 7, scanning is performed with the excitation light L1 and the measurement light L3 in a main scanning direction (X direction) illustrated in FIG. 7, and the scanning in the main scanning direction is sequentially repeated along a sub-scanning direction (Y direction). In addition, the position markers 16 are formed in the form of dots at predetermined intervals in the sub-scanning direction perpendicular to the main scanning direction. It is preferable that the interval between the dots of the position marker 16 is set to be the same as the scanning interval in the sub-scanning direction.

Figure 8:
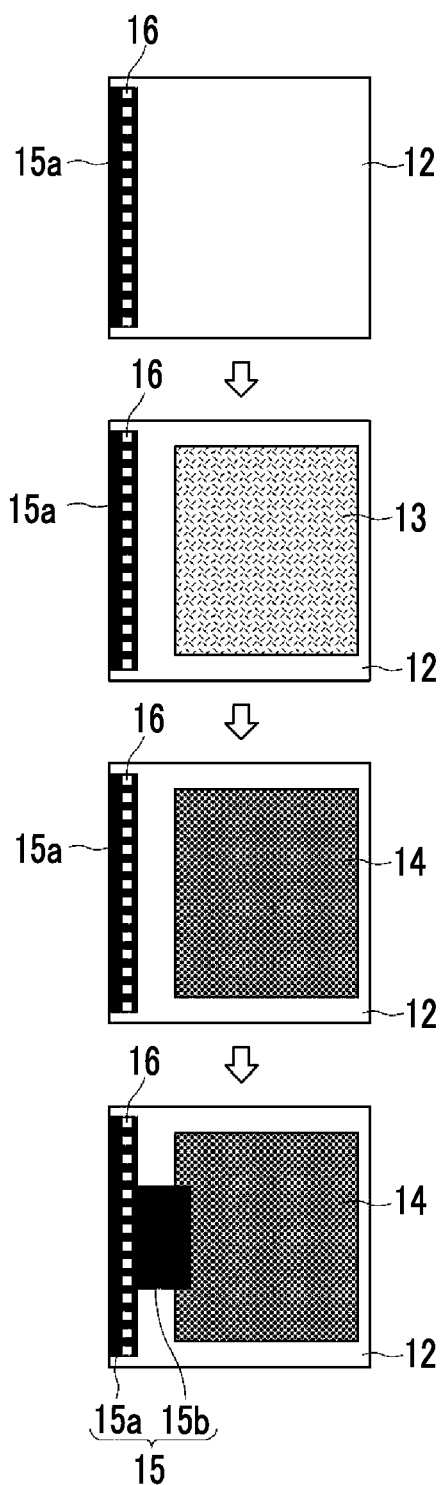
FIG. 8 is a diagram illustrating each process of a method of manufacturing the measurement device illustrated in FIG. 7.

Here, a method of manufacturing the measurement device 10 illustrated in FIG. 7 will be described with reference to FIG. 8. Meanwhile, here, a method of forming the position markers 16 will be mainly described.

First, an electrode pattern with a marker 15a in which a portion of each of the position markers 16 is configured to be a void is formed by photolithography and lift-off is formed on an end of one side of the plate-like substrate body 12.

Subsequently, after the electrode pattern with a marker 15a is formed, the fine concavo-convex structure 13 constituted by boehmite is formed in the same manner as the above-described embodiment. In addition, the metal fine concavo-convex structure layer 14 is formed by vapor-depositing a metal film on the fine concavo-convex structure 13.

Subsequently, a connection electrode pattern 15b is formed between the electrode pattern with a marker 15a and an end of the surface of the metal fine concavo-convex structure layer 14 by vapor deposition, and thus the voltage application electrode 15 constituted by the electrode pattern with a marker 15a and the connection electrode pattern 15b is formed.

Figure 9A:
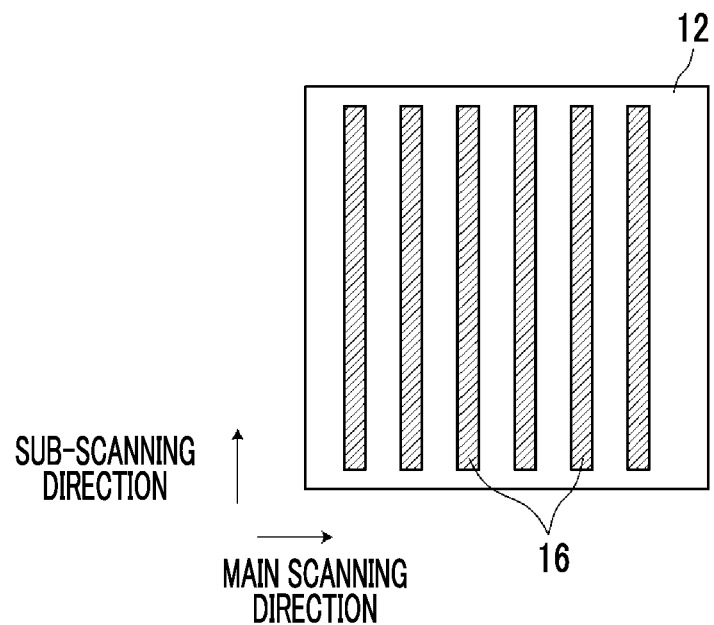
FIG. 9A is a diagram illustrating a position marker according to another embodiment.
Figure 9B:
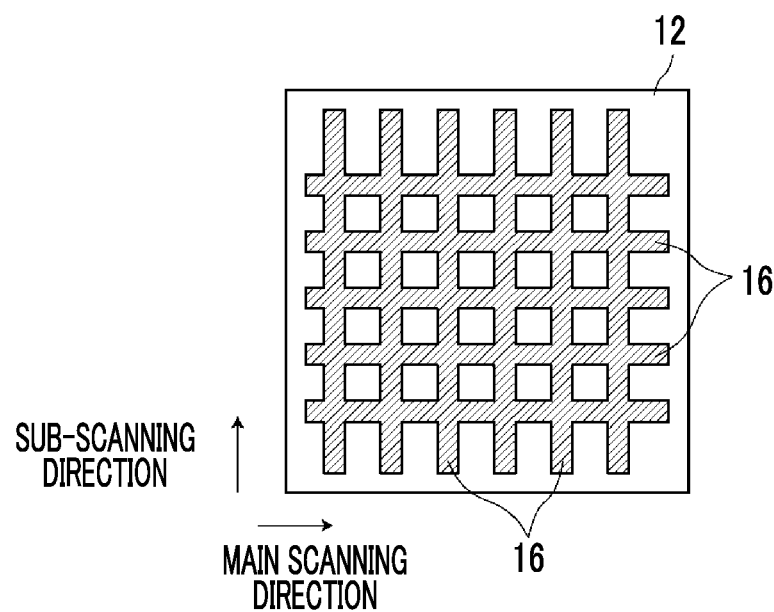
FIG. 9B is a diagram illustrating a position marker according to another embodiment.

Meanwhile, a pattern other than the pattern illustrated in FIG. 7 may be used as the pattern of the position marker 16. In addition, a location in which the position marker 16 is formed is not limited to the voltage application electrode 15. For example, a stripe-like metal pattern as illustrated in FIG. 9A may be formed in the entire substrate body 12, and a lattice-like metal pattern as illustrated in FIG. 9B may be formed in the entire substrate body.

Figure 10:
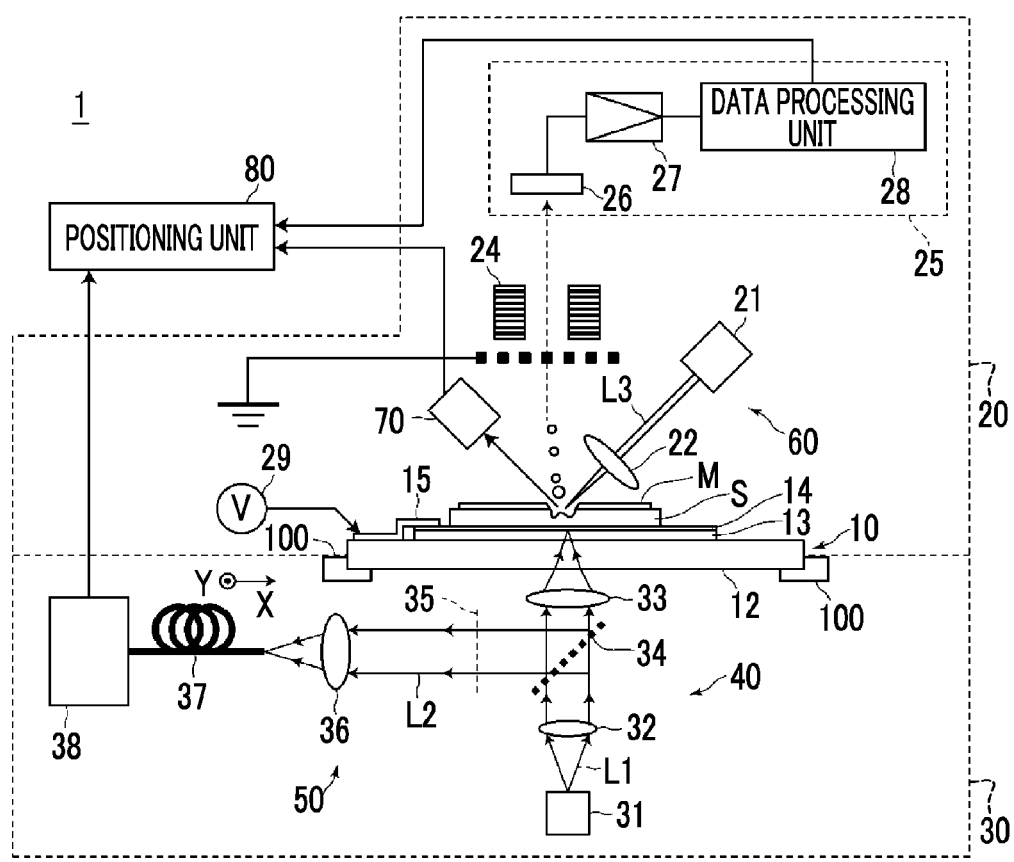
FIG. 10 is a diagram illustrating a schematic configuration of a measurement apparatus according to another embodiment of the present invention.

FIG. 10 illustrates a configuration of the measurement apparatus 1 that detects the position markers 16 provided in the measurement device 10 as described above and performs the positioning of measurement results in the respective measurement systems on the basis of a result of the detection.

In the Raman scattered light measurement system 30 of the measurement apparatus 1 illustrated in FIG. 10, up to the range of the voltage application electrode 15 provided with the position markers 16 of the measurement device 10 is scanned with the excitation light L1, reflected light from the voltage application electrode 15 provided with the position markers 16 is detected by the spectroscope 38, and a result of the detection is input to a positioning unit 80 similar to the detection result of the Raman scattered light. Meanwhile, the reflected light from the voltage application electrode 15 is mostly cut by the notch filter 35, but is not completely cut. A portion of the reflected light passes through the notch filter, and thus can be detected by the spectroscope 38.

In the positioning unit 80, a Raman spectrum distribution image of a specific substance is created on the basis of a Raman spectrum measured at each scanning point. At this time, the Raman spectrum distribution image is created so that an image of the position marker 16 is disposed at a position which is set in advance on a coordinate space of the Raman spectrum distribution image.

On the other hand, in the mass spectrometry measurement system 20 of the measurement apparatus 1 illustrated in FIG. 10, a photodetector 70 detecting reflected light of the measurement light L3 on the measurement device 10 is provided.

In addition, up to the range of the voltage application electrode 15 provided with the position markers 16 of the measurement device 10 is scanned with the measurement light L3, reflected light from the voltage application electrode 15 provided with the position markers 16 is detected by the photodetector 70, and a result of the detection is input to the positioning unit 80.

In the positioning unit 80, a mass spectrum distribution image of a specific substance is created on the basis of a mass spectrum measured at each scanning point. At this time, the mass spectrum distribution image is created so that an image of the position marker 16 is disposed at a position which is set in advance on a coordinate space of the mass spectrum distribution image.

In addition, the positions which are set in advance on the coordinate spaces of the above-mentioned two distribution images are set to be the same position on the respective coordinate spaces, and thus it is possible to perform the positioning of the two distribution images.

The two distribution images generated by the positioning unit 80 are output to a predetermined display device (not shown), and are displayed on a display device.

Meanwhile, in the above description, a reflection pattern of a void formed as the position marker 16 in the voltage application electrode 15 is detected. However, the position marker 16 is not limited to the void, and may be formed of a material having higher reflectance or absorptance with respect to the excitation light L1 and the measurement light L3 than that of the voltage application electrode 15. Alternatively, the position marker 16 may be formed of a material emitting fluorescent light by the irradiation with the excitation light L1 and the measurement light L3. However, when the position marker 16 is formed of the void as described above, the position marker 16 can be formed simultaneously with a process of manufacturing the voltage application electrode 15, and thus it is not necessary to provide a new manufacturing process, which leads to a more preferable result.

Meanwhile, in the measurement apparatus 1 of the above-described embodiment, mass spectrometry is performed, and Raman scattered light is detected. However, the present invention is not limited to the detection of the Raman scattered light, and fluorescent light may be detected by a plasmon enhanced fluorescence detection method. Further, it is possible to use the measurement device 10 mentioned above not only in measuring Raman scattered light and fluorescent light but also in an apparatus and method for measuring Rayleigh scattered light, Mie scattered light, or a second harmonic which is generated from a substance in the vicinity of a metal film irradiated with the excitation light L1.

What is claimed is:

1. A measurement device comprising:
   a transparent dielectric substrate that is constituted of a dielectric having a transparent fine concavo-convex structure in a surface thereof; and
   a metal fine concavo-convex structure layer that is configured by forming a metal film on a surface of the fine concavo-convex structure,
   wherein the metal fine concavo-convex structure layer allows electrical conduction within the metal fine concavo-convex structure layer, and
   wherein a voltage application electrode for applying a voltage to the metal fine concavo-convex structure layer is provided.

2. The measurement device according to claim 1, wherein a surface resistivity of the metal fine concavo-convex structure layer is equal to or less than $10^7$ $\Omega$/cm.

3. The measurement device according to claim 1, wherein the fine concavo-convex structure is formed of boehmite.

4. The measurement device according to claim 1, wherein the metal film is formed of at least one metal selected from a group consisting of Au, Ag, Cu, Al, Pt, and an alloy containing the metal as a main component.

5. The measurement device according to claim 1, wherein a position marker for indicating a measurement position is provided.

6. The measurement device according to claim 5, wherein the position marker is provided in the voltage application electrode.

7. The measurement device according to claim 6, wherein the position marker is a void provided in the voltage application electrode.

8. A measurement apparatus comprising:
   the measurement device according to claim 1;
   a first light irradiation unit that irradiates the metal film of the measurement device with first light from the transparent dielectric substrate side and generates an enhanced optical electric field on a surface of the metal film by an optical electric field enhancing effect of a localized plasmon induced to the surface by the irradiation; a light detection unit that detects light which is generated by the irradiation of the measurement device with the first light and which is emitted from the transparent dielectric substrate side;
   a second light irradiation unit that irradiates a specimen installed on a surface of the metal fine concavo-convex structure layer and a matrix agent supplied onto the specimen with second light from a side opposite to the side of the irradiation with the first light in a state where a voltage is applied to the metal fine concavo-convex structure layer through the voltage application electrode, and desorbs an analysis target substance for mass spectrometry in the specimen from the surface by the irradiation; and
   an analysis unit that detects the desorbed analysis target substance to thereby analyze the mass of the analysis target substance.

9. The measurement apparatus according to claim 8, further comprising a scanning mechanism that two-dimensionally scans an upper portion of the measurement device with the first light and the second light.

10. The measurement apparatus according to claim 8, wherein a position marker for indicating a measurement position is provided; and
    a positioning unit that performs positioning of an optical spectrum distribution image generated on the basis of a detection result of the light detection unit and a mass spectrum distribution image generated on the basis of an analysis result of the analysis unit, on the basis of a detection result of the position marker provided in the measurement device.

11. The measurement apparatus according to claim 8, further comprising a voltage application unit that applies a voltage to the voltage application electrode of the measurement device.

12. A measurement method comprising:
    irradiating the metal film of the measurement device according to claim 1 with first light from the transparent dielectric substrate side;
    detecting light emitted from the transparent dielectric substrate side by generating an enhanced optical electric field on a surface of the metal film by an optical electric field enhancing effect of a localized plasmon induced to the surface by the irradiation;
    irradiating a specimen installed on a surface of the metal fine concavo-convex structure layer and a matrix agent supplied onto the specimen with second light from a side opposite to the side of the irradiation with the first light in a state where a voltage is applied to the metal fine concavo-convex structure layer through the voltage application electrode;
    desorbing an analysis target substance for mass spectrometry in the specimen from the surface by the irradiation; and detecting the desorbed analysis target substance to thereby analyze the mass of the analysis target substance.

* * * * *